United States Patent
Spencer

(10) Patent No.: US 6,726,474 B2
(45) Date of Patent: Apr. 27, 2004

(54) REMOVABLE SELF-LIGATING MODULE FOR ORTHODONTIC BRACKETS

(76) Inventor: William A. Spencer, 8800 Kings Lynn La., Louisville, KY (US) 40220

( * ) Notice: Subject to any disclaimer, the term of this patent is extended or adjusted under 35 U.S.C. 154(b) by 10 days.

(21) Appl. No.: 10/199,746

(22) Filed: Jul. 19, 2002

(65) Prior Publication Data

US 2004/0013995 A1 Jan. 22, 2004

(51) Int. Cl.[7] .................................................. A61C 3/00
(52) U.S. Cl. ........................................... 433/11; 433/10
(58) Field of Search ............................. 433/10, 11, 13, 433/14

(56) References Cited

U.S. PATENT DOCUMENTS

| | | | |
|---|---|---|---|
| 4,149,314 A | * | 4/1979 | Nonnenmann |
| 4,712,999 A | | 12/1987 | Rosenberg |
| 4,975,052 A | | 12/1990 | Spencer et al. |
| 5,380,197 A | | 1/1995 | Hanson |
| 5,456,599 A | | 10/1995 | Hanson |
| 5,586,882 A | | 12/1996 | Hanson |
| 5,630,715 A | | 5/1997 | Voudouris |
| 5,630,716 A | | 5/1997 | Hanson |
| 5,685,711 A | | 11/1997 | Hanson |
| 5,711,666 A | | 1/1998 | Hanson |
| 5,738,513 A | | 4/1998 | Hermann |
| 5,857,849 A | | 1/1999 | Kurz |
| 5,906,486 A | | 5/1999 | Hanson |
| 5,908,293 A | * | 6/1999 | Voudouris ................ 433/10 |
| 5,993,207 A | | 11/1999 | Spencer |
| 6,042,373 A | | 3/2000 | Hermann |
| 6,042,374 A | | 3/2000 | Farzin-Nia et al. |
| 6,071,118 A | | 6/2000 | Damon |
| 6,071,119 A | | 6/2000 | Christoff et al. |
| 6,193,508 B1 | | 2/2001 | Georgakis |
| 6,302,688 B1 | | 10/2001 | Jordan et al. |
| 6,325,622 B1 | | 12/2001 | Kelly et al. |

* cited by examiner

*Primary Examiner*—Cary E. O'Connor
(74) *Attorney, Agent, or Firm*—Dorr, Carson, Sloan, Birney & Kramer, P.C.

(57) ABSTRACT

A self-ligating module for removable attachment to a conventional orthodontic bracket includes a stem removably securable in the vertical slot in the bracket and a clip pivotably secured to the head of the stem. The clip can pivot between an open position in which the archwire slot of the bracket is open to receive an archwire, and a closed position in which the archwire is secured in the archwire slot by the clip. The module allows conventional orthodontic brackets to be selectively modified so as to become self-ligating brackets. The module can be readily removed when the self-ligating feature is not needed.

8 Claims, 4 Drawing Sheets

REMOVABLE SELF-LIGATING MODULE FOR ORTHODONTIC BRACKETS

BACKGROUND OF THE INVENTION

1. Field of the Invention

The present invention relates generally to the field of orthodontic brackets. More specifically, the present invention discloses a removable module that can be attached to a conventional orthodontic bracket to provide a selectively removable self-ligation capability.

2. Statement of the Problem

The orthodontic tooth brace (more correctly known as the orthodontic bracket) is a central component of current, conventional orthodontic treatment practice. For an orthodontic patient's treatment, an orthodontist will typically attach brackets to each of a patient's teeth to serve as the primary receptors of corrective tooth-positioning forces. Such corrective forces are transmitted through brackets to the crowns of the teeth and then translated to the roots of teeth where they elicit certain osteogenic responses from the adjacent supportive bone, allowing the slow corrective repositioning of teeth according to the vector sum of the combined corrective forces applied to the bracket and tooth.

FIG. 1 is front perspective view of a typical orthodontic bracket assembly. The bracket 30 has a bonding pad for secure attachment to a tooth 10. The rectangular shaft extending through the bracket 30 represents a section of an archwire 20. An elastomeric ligature 31 is retained under the four tie wings 32 of the bracket 30. The ligature 31 serves to retain the archwire 20 in the archwire slot of the bracket 30.

The orthodontic bracket was first developed by Dr. Edward Hartley Angle in the late 1800's and in spite of significant improvement in design, materials and manufacturing processes that have occurred since Dr. Angle's time, the bio-mechanical functioning of orthodontic brackets remains essentially unchanged. Central to the functioning of an orthodontic bracket is the archwire slot. The archwire slot is a generally horizontal, outwardly opening, rectangular-shaped trough formed in the structure of a bracket that accepts a separate, correspondingly rectangular-shaped archwire. The orthodontic bracket taught by Dr. Angle is known as the "Edgewise" bracket, Edgewise being a descriptive term referring to the rectangular interfit of the archwire slot and the archwire typically employed for Edgewise orthodontic therapy. The archwire is rectangular in cross-section and is retained in the rectangular-shaped archwire slot by ligation means that positively hold an archwire fully constrained and seated within the bracket's archwire slot. During orthodontic treatment, an archwire normally extends around a patient's arch and is ligated into the archwire slots of all of the brackets of a patient's upper or lower dental arch. A patient will normally be treated with one set of brackets and an archwire for the upper dental arch and another set for the lower.

As can be appreciated, the Edgewise interfit of the wire and the slot allows for a semi-rigid connection between the archwire slot and the archwire. Being engaged in this way, an archwire can transmit corrective forces to the structure of a tooth that serve to cause that tooth to be uprighted to a desirable inclination, which is known as correction in terms of "torque." A tooth can also be uprighted laterally, known as correction in terms of "angulation." An archwire can impart corrective forces known as "rotation" which cause a tooth to desirably rotate around its central axis. Other corrective forces can be transmitted from an archwire to a tooth through its corresponding bracket that tend to intrude or extrude a tooth into or out of it's bony support. Such corrective forces are known as "intrusive" or "extrusive." An archwire can influence a tooth to move bodily outward or inward, and such forces are said to position a tooth in terms of "prominence." Since the Edgewise relationship between an archwire and a bracket's archwire slot does not preclude a relative sliding movement between an archwire and a bracket, other tractive or compressive forces may be applied to a tooth that urge a tooth to desirably slide along the mesio-distal extent of an archwire into a new position. Over the course of orthodontic treatment, patient's teeth are moved to corrected positions through a combination of most, if not all of these forces acting simultaneously on the teeth.

At the beginning of orthodontic treatment, a patient's teeth are of course out of alignment. Since the exact location and orientation of a bracket on a patient's teeth ultimately determines the final treated position of a tooth relative to an archwire, the skill with which an orthodontist can attach brackets at ideal positions and orientations on the teeth is paramount. To fully appreciate this, the brackets are first visualized on teeth that are ideally positioned at the conclusion of treatment. All bracket slot walls are aligned and coincident so that a full-size, naturally-curving archwire lies passively in all of the slots. Next, imagine the archwire removed and the teeth gradually moved out of position, carrying their brackets with them until the teeth are as malaligned as they were prior to treatment. The slots have of course become as malaligned as the teeth. This is in fact the condition that actually exists when brackets are properly sited on the crowns of a patient's teeth.

After brackets have been placed on the teeth at the start of orthodontic treatment, an orthodontist ligates the first of a series of sequential archwires into the archwire slots of the brackets. Commercially-available archwires are manufactured to a form that mirrors the natural gentle curve of the human dentition. As described above however, the archwire slots at the beginning of treatment are as malaligned as the teeth they are attached to. Because of this, the archwire may be required to undergo sometimes severe bending and zig-zagging as the orthodontist ligates the archwire into one archwire slot after another. In this manner, the act of deflecting an otherwise flat, elegantly curving archwire away from its passive form causes energy to be stored in the archwire just as energy can be stored in a spring. It is the slow dissipation of this stored energy the drives the slow biological responses allowing the teeth to desirably reposition.

As can be appreciated, at the onset of treatment, one tooth may be intruded, distal-ligually rotated and lingually inclined for example, and an adjacent tooth may be super-erupted, mesio-lingually rotated and flared labially. In such a case, an archwire passing through the archwire slots of the two brackets attached to the teeth of this example must undergo a severe deflection. Later during the course of treatment, after the two teeth in the example above have responded and moved into a somewhat closer alignment, the severity of the required deflection will be lessened. To exploit this, and to custom-tailor the forces applied to teeth as treatment progresses, orthodontists will typically begin a patient's treatment with an archwire that has mechanical properties that include a relatively low tensile strength of about 140 KSI UTS, combined with a modulus of elasticity in the range of 5,000,000 to 12,000,000. Such wires are compliant and can tolerate such severe deflections encountered at the beginning of treatment without taking a permanent set, while still being capable of delivering physiologically-effective tooth-moving forces. Such initial archwires are typically round in cross-section and are not intended to mechanically take advantage of the rectangular Edgewise configuration of the archwire slot. Archwires fitting the above descriptions may for example be 0.012 inch in diameter and formed from a relatively soft temper stainless steel alloy, or 0.016 inch diameter super-elastic nickel titanium alloy. Other wires falling into this beginning category may be formed from a braided, multi-strand cable.

As treatment progresses, the severe deflections encountered at the beginning of treatment become less severe and an orthodontist can progress to a second and a third of a series of archwires used for a patient's ongoing treatment. Mid-treatment wires tend to be somewhat stiffer, having both a higher tensile strength and a higher modulus of elasticity. Such wires ideally deliver the same physiologically effective forces as the initial wires, but since they encounter less strain or deflection, they must be somewhat stiffer in order to maintain physiologically-effective tooth-moving force levels.

Once a set of treatment conditions have been achieved in which there is a normal orthopedic relationship between the upper and lower arches, and all of the teeth have been generally intruded or extruded through a step termed "leveling" and the teeth have been bodily moved labially or lingually into general compliance with an anatomically-normal arch form, an orthodontist will begin what is known as the finishing phase of treatment. The goal of the finishing phase is to bring the teeth into their ideal and final aesthetic positions, in ideal relations to each other and with stable interproximal contacts, and with the roots parallel and positioned properly over the supporting bone. Even though earlier steps may have utilized Dr. Angle's Edgewise philosophy and its use of rectangular cross-section archwires within the rectangular archwire slot, it is the finishing phase where the principles of Edgewise therapy are brought to bear in finishing a patient's treatment.

Typically an orthodontist will first employ a less than full-sized archwire having a rectangular or square cross-section at the beginning of the finishing phase. The bracket's archwire slot may, for example, have internal dimensions of 0.018 inch wide by 0.025 inch deep. The first finishing wire may exhibit a square cross-section measuring 0.016 per side. As can be appreciated, such a slot-to-wire relationship permits some "slop". Even though this relationship intentionally introduces some slop, the combination nonetheless is capable of generating initial tooth-torqueing forces in the direction needed for final tooth alignment. Further, the combination drives a finer degree of alignment in terms of angulation, prominence and rotation. Another reason for this sequential or progressive approach of sequentially larger and stiffer archwires is that if an orthodontist were to proceed directly to a full-sized finishing archwire, several undesirable consequences might be encountered. First, by attempting to prematurely install a full-sized finishing archwire into the archwire slots, higher than physiologically desirable forces can be generated resulting in pain and discomfort for the patient, and trauma to the periodontal membrane surrounding the roots of the teeth. Additionally, in some cases, the structural integrity of a bracket or other oral hardware may be exceeded, causing distortion or breakage. Again, orthodontists typically work toward a point in treatment when a full-sized finishing wire can be installed in the mouth without excessive discomfort to the patient and without placing excessive structural loads on the orthodontic hardware.

A typical full-size finishing archwire is sized to generally fully fill a bracket's archwire slot leaving only sufficient clearance for insertion. Such archwires are generally very stiff, having a tensile strength of about 310 KSI UTS and a modulus of elasticity approaching 30,000,000. As can be appreciated, all of the archwire slots accepting a finishing wire must be very nearly aligned to allow the finishing wire to be installed without the problems of patient discomfort and excessive stresses.

Throughout the foregoing, it can be appreciated that orthodontic treatment is initiated with archwires exhibiting a low spring rate and high deflection, and sequentially superceded with subsequent archwires that exhibit progressively higher spring rates at lower deflections. In practice, handling and manipulation of the ligation means can further moderate or regulate the forces that the archwires transmit to the teeth. For example, at the stage described above where the first of the Edgewise finishing wires is inserted, an orthodontist may elect to not fully ligate the wire into an archwire slot. Partial engagement of an archwire in an archwire slot may be achieved through the use of elastomeric ligatures. Elastomeric ligatures are typically molded from a urethane elastomer, which also exhibits spring-like tractive properties. If an archwire is not fully seated in the slot due to a tooth being undesirably and excessively rotated for example, the tractive forces of the elastomeric ligature combine with the spring properties of the archwire to urge rotational correction, as shown in FIG. 1 for a maxillary central tooth.

Alternatively, stainless steel ligatures may be used. These are formed from a dead-soft 0.009 inch through 0.012 inch diameter round wire. The steel ligature is tied around the tie wings of a bracket and over the archwire thus retaining the archwire in its slot. Once tied, the loose ends of the wire are twisted and the twisted section is then tucked under the wings out of the way to avoid laceration of the soft tissues of the tongue or cheeks. An orthodontist has the option of tying such a steel ligature tightly or less tightly. In cases where a steel ligature is intentionally tied less tightly, it can usually be fully tightened at the patient's next office visit after the tooth has further responded. So again, sequential ligation can be used in conjunction with sequential archwires as the teeth slowly respond and desirably reposition.

The Siamese-type Edgewise bracket, a variation of Dr. Angle's original Edgewise bracket, provides yet other ligation options. Since a Siamese-type Edgewise bracket has one set of distal tie wings and a second set of mesial tie wings, either set may be used alone for ligation. Selective ligation of only one set of tie wings can facilitate movement of a particularly mal-rotated tooth. For example, if a tooth exhibits a significant distal-lingual rotation, only the distal wings of its bracket may be engaged by a ligature extending over the archwire. Contact of the archwire at the mesial end of the archwire slot combined with the tractive forces of a ligature pulling the tooth toward the archwire at its distal extent creates a particularly effective mechanical couple providing a significant mechanical advantage of forces acting to expedite correction of the undesirable rotation.

As can be appreciated, a large portion of an orthodontist's time spent with his patients as well as a large portion of his staff's duties revolve around routine ligation tasks and the removing and replacing of archwires. The time required to remove the previous archwire and install a subsequent one is considerable. In particular, the placing of individual ligatures over the tie wings of the brackets of each and every tooth is a very exacting and time-consuming procedure.

The advent of the elastomeric ligature described above, beginning about 1975 has reduced the time required to change a patient's archwire because the twisting, cutting and tucking steps required by the older methods using steel ligatures are eliminated, but even using elastomeric ligatures, a large percentage of the total time a patient is seen by an orthodontist and staff remains associated with the routine steps of ligation.

An improvement over, or an alternative to the time-consuming ligation step has long been sought. U.S. Pat. No. 4,248,588 (Hanson) disclosed an all-metallic, self-ligating bracket. Hanson taught a new type of bracket assembly that incorporates a retaining clip capable of being slidingly positioned in a fully open or fully closed position. In the open position, an archwire can be inserted into Hanson's bracket and, in the closed position, the archwire will be retained. The archwire-contacting points of the spring-temper sliding clip taught by Hanson aggressively hold an archwire in position in a slot, but it is also capable of limited flexing and limited torsion. Such flexing and torsioning capabilities act in a manner similar to the desirable spring property of elastomeric ligatures described above, and the spring clip would continuously act to urge the archwire to a fully-seated position. Such a self-ligating bracket as taught by Hanson could accommodate an excessively rotated tooth for example and facilitate correction in terms of rotation through dissipation of the energy stored in the spring clip of his innovative bracket. Subsequent improvements to Hanson's bracket brought about a slight curvature to the archwire-contacting portions of Hanson's spring clip that further enhanced his self-ligating bracket to continuously act to desirably position a tooth by the constant working action of the spring clip against an archwire.

Another innovation in the field of self-ligating brackets is seen in U.S. Pat. No. 5,474,445 (Voudouris). Voudouris introduced an all-metallic self-ligating bracket assembly configured to achieve a fully open and fully closed archwire retaining action through the use of a pivoting clip rather than a sliding clip as taught by Hanson. Voudouris' clip positively snapped closed and therefore lacked the dynamic "working" quality of Hanson's bracket. More importantly however, Voudouris provided the feature of self-ligation in combination with a Siamese-type configuration through the '445 patent and subsequent improvements. The features of Voudouris' bracket afforded the desirable selective ligation option of conventional brackets where either a distal or a mesial portion of the Voudouris bracket could be ligated if needed to achieve a rotational couple, thereby eliminating the need for the spring clip to actively function as taught by Hanson.

Other improvements to the art of self-ligating brackets can be found in the subsequent patent art relating to self-ligating brackets. In commercial terms and as a group, most major orthodontic manufacturers currently offer self-ligating bracket systems with various improvements over the two basic configurations brought forth by Hanson and Voudouris. From the orthodontist's point of view, the availability of self-ligating brackets clearly reduces the amount of chair time required to change an archwire and thus provides the sought after solution to the excessive time required to deliver orthodontic care. In addition to these advancements, self-ligating brackets, being all-metallic, avoid growing concerns within the orthodontic profession over the safety and biocompatibility of the otherwise popular urethane elastomeric ligatures, which are suspected as providing a harbor for oral bacteria and the biocompatibility of the urethane polymer itself has been questioned.

In spite of the many advantages brought about by the self-ligating bracket, self-ligating brackets pose several new problems and disadvantages, which are successfully addressed by the present invention. As can be appreciated, self-ligating brackets inherently consist of multiple parts whereas conventional brackets are manufactured as monolithic structures. Because self-ligating brackets have additional structure associated with multiple parts, and because self-ligating brackets embody additional features to support the capability of self-ligatability, they are inherently more bulky and generally extend further from the tooth surface than conventional brackets. Orthodontic patients are typically young teens going through the years of self-consciousness. From the patient's point of view, larger, more prominent brackets are undesirable from an aesthetic and a self-image standpoint. In addition, due their generally increased bulk as described above, current commercially available self-ligating brackets generally cause greater irritation to the insides of the cheeks and lips of an orthodontic patient. From the patient's point of view, there are few if any tangible advantages to being treated with self-ligating brackets.

Another undesirable quality of conventional self-ligating brackets is that the pace with which archwires are sequentially replaced during the course of orthodontic treatment is not constant. Typically, archwires are changed much more frequently during one phase of treatment compared to another. The advantages of the self-ligating brackets therefore are realized by an orthodontist to the greatest extent during phases of treatment during which more frequent archwire changes are required than during other phases, yet a patient may endure discomfort continuously during the entire duration of his or her treatment.

Currently, once an orthodontist chooses to treat a particular case with self-ligating brackets, those brackets are bonded to the teeth at the start of treatment and remain in place during the entire duration of treatment. Certain phases of treatment, or certain steps required by some patients' treatment may call for certain groups of brackets to be bypassed and unengaged to an archwire for a time. Certainly during such times there are clearly no advantages for either the patient or the doctor regarding the use of self-ligating brackets. As described above, patients being treated with self-ligating brackets commonly experience higher degrees of irritation and may be also be self-conscious about wearing more prominent and larger, more visible brackets. Again, for the patient, such problems may persist for the entire duration of treatment, which may be 26 to 30 months. So as can be appreciated, the advantages of self-ligating bracket use may be significant but sporadic only for the orthodontist, and for a patient there are no advantages, and in fact use of self-ligating brackets poses potential disadvantages.

3. Solution to the Problem. The present invention provides a removable module that can be readily attached to conventional orthodontic brackets to selectively provide a self-ligating feature. This allows conventional orthodontic brackets to be selectively modified so as to become self-ligating brackets, and then the modules can be removed when not needed.

SUMMARY OF THE INVENTION

This invention provides a self-ligating module for removable attachment to a conventional orthodontic bracket. The module includes a stem removably securable in the vertical slot in the bracket and a clip pivotably secured to the head of the stem. The clip can pivot between an open position in which the archwire slot of the bracket is open to receive an archwire, and a closed position in which the archwire is secured in the archwire slot by the clip. The module allows conventional orthodontic brackets to be selectively modified so as to become self-ligating brackets. The module can be readily removed when the self-ligating feature is not needed.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
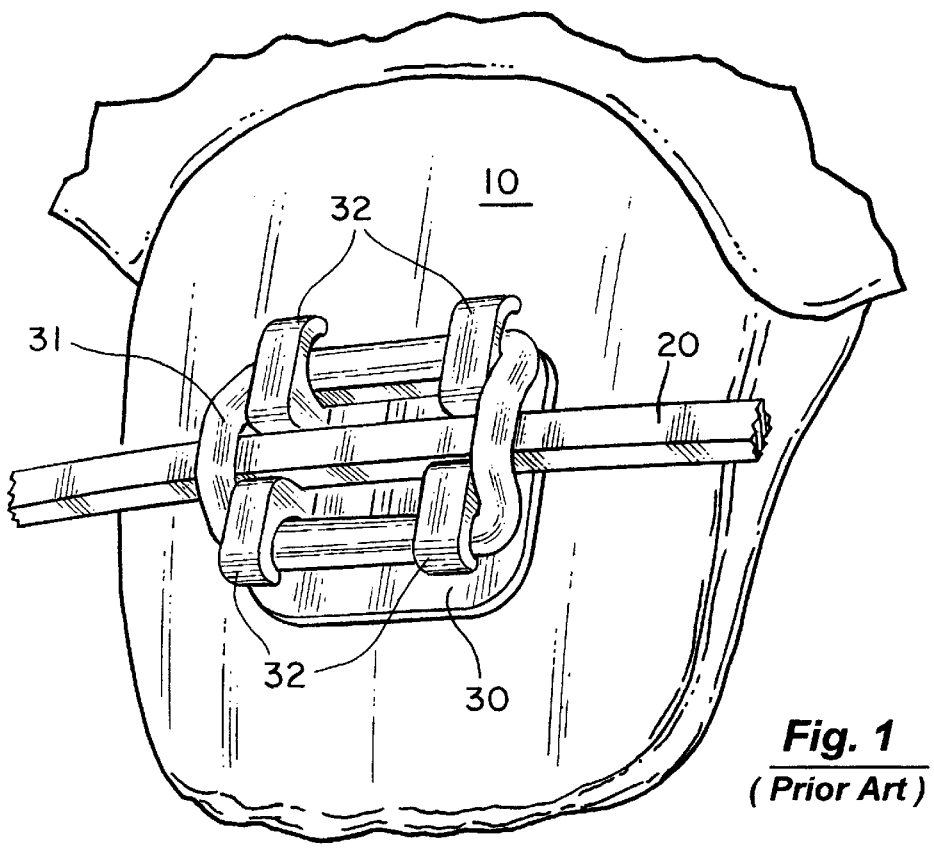
FIG. 1 is a front perspective view of a conventional orthodontic bracket 30 mounted on a maxillary central tooth 10 and having an elastomeric ligature 31 holding an archwire 20 in the archwire slot of the bracket 30.

The self-ligating module 40 in the present invention is intended for use with a conventional orthodontic bracket 30. The bracket 30 typically has a base 38 that can be bonded to the labial surface of a maxillary central tooth 10, as shown in FIG. 1. Four tie wings 32 extend outward from the base and define a horizontal archwire slot 34 to receive an archwire 20. The bracket 30 shown in FIG. 1 is intended for use on a maxillary central tooth, while the tie wings 32 on the bracket 30 shown in FIG. 2 are intended for use on a lower anterior tooth.

Figure 2:
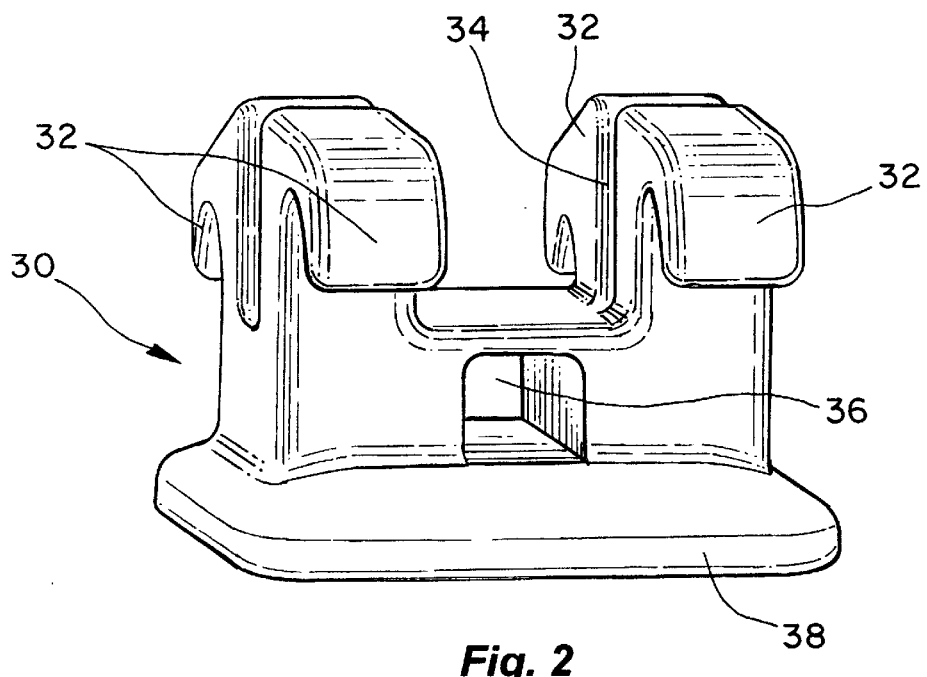
FIG. 2 is a perspective view of a conventional orthodontic bracket 30 for a lower anterior tooth having a vertical slot 36.

The bracket 30 also includes a vertical slot 36 shown in FIG. 2. Vertical slots are well known and have been available in various forms as a feature of orthodontic brackets since the 1950's. The vertical slot 36 is oriented perpendicular to the main archwire slot 34 of the bracket 30 and is positioned as close to the tooth 10 as possible. Orthodontic manufacturers have standardized the dimensions of vertical slots and full bracket systems are offered with vertical slots. Vertical slots are generally intended to accept a family of vertically-inserting auxiliaries used temporarily by orthodontists to effect uprighting and rotations of teeth. In addition, the vertical slot feature of conventional orthodontic brackets is used in many creative ways by orthodontists other than for use with vertically-inserting auxiliaries. An orthodontist can even place a ligature wire through the vertical slot to bolster the conventional ligatures if needed.

Some conventional orthodontic brackets have a slightly rhomboid shape, which results in a slot that is slightly off vertical. Thus, the phrase "vertical slot" as used herein should be interpreted to include a rhomboid bracket slot and any other bracket slot that is substantially vertical in orientation.

Figure 3:
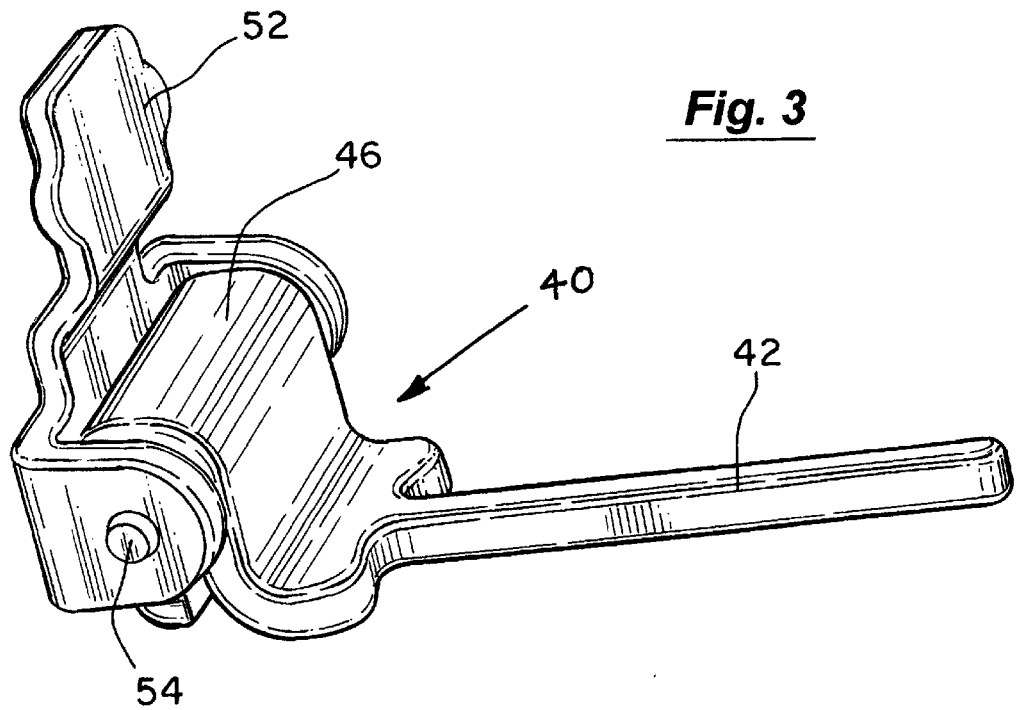
FIG. 3 is a perspective view of the removable self-ligating module 40 with the pivoting spring clip 52 in its open position.
Figure 4:
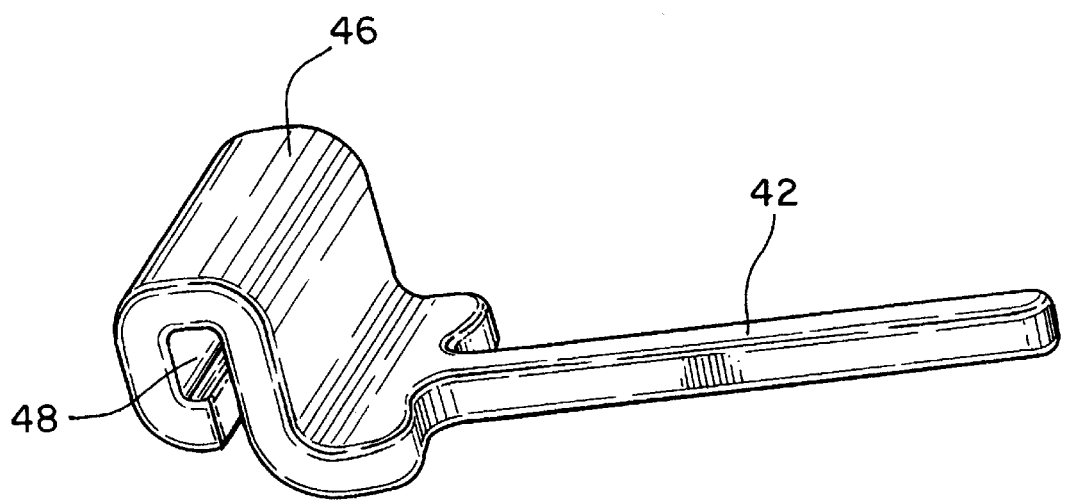
FIG. 4 is a perspective view of the stem 42 of the self-ligating module 40.
Figure 5:
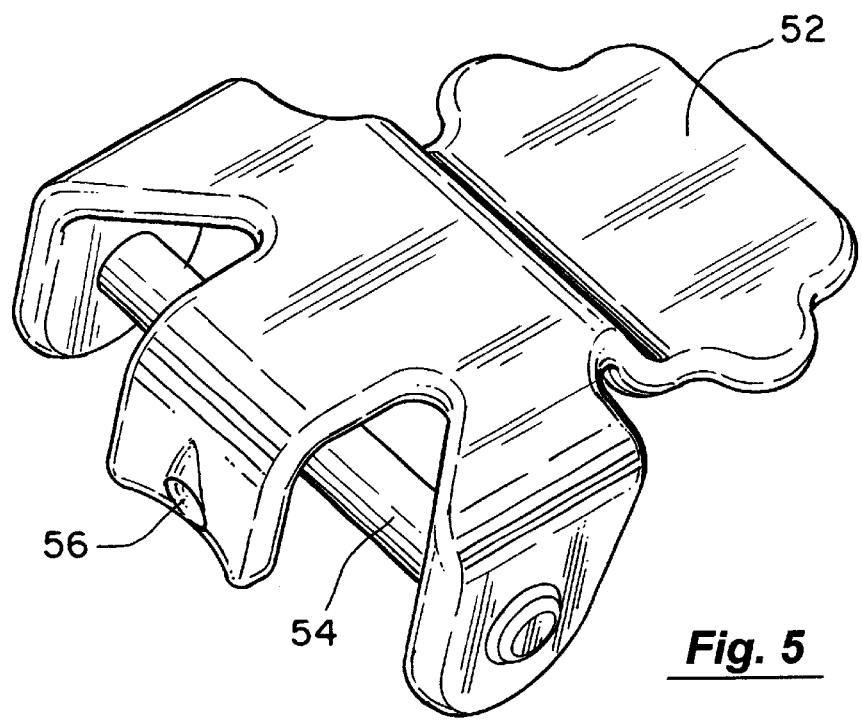
FIG. 5 is a perspective view of the pivoting spring clip 52 of the self-ligating module 40.
Figure 6:
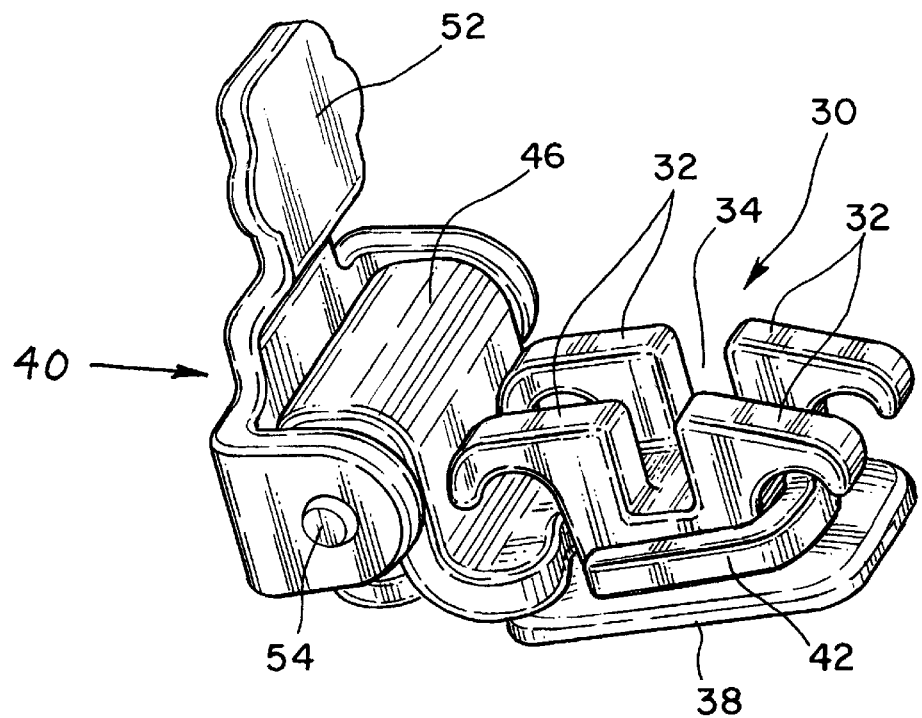
FIG. 6 is a perspective view of the self-ligating module 40 inserted into a bracket 30 with the pivoting spring clip 52 in its open position, and with the stem 42 bent to secure the self-ligating module 40 to the bracket 30.

FIG. 3 is a perspective view of the removable self-ligating module 40. Its major components are a stem 42, shown in FIG. 4, and a pivoting spring clip 52, shown in FIG. 5. The stem 42 has dimensions allowing it to be freely inserted through the vertical slot 36 of the bracket 30 with the end of the stem 42 extending beyond opposite end of the vertical slot 36, as shown for example in FIG. 7. Typically, the stem 42 is inserted in a vertical slot 36 from the gingival side of a bracket 30, so that the end of the stem 42 extends beyond the occlusal end of the vertical slot 36. Following its insertion through the vertical slot 36, the stem 42 is removably secured in the vertical slot 36 by bending the end of the stem 42 so that the stem 42 cannot be retracted through the vertical slot 36. For example, the module 40 can be securably retained in the bracket 30 through the double bending of the protruding end of the stem 42 around either side of the bracket 30, as shown in FIG. 6. The end of the stem 42 can be straightened, or the bent portion may be cut off, to remove the stem 42 from the vertical slot 36 in which it has been inserted when no longer needed.

In the preferred embodiment of the present invention, the stem 42 and the vertical slot 36 are correspondingly configured to restrict rotational movement therebetween. More particularly, all or at least a portion of the stem 42 that is insertable in the vertical slot 36 may have a polygonal (e.g. rectangular) cross-section and all or at least a portion of the vertical slot 36 in which the stem 42 is received may have a corresponding polygonal (e.g. rectangular) cross-section.

The head 46 of the stem 42 remains outside of the vertical slot, and can be equipped with a shoulder contoured to abut the body of the bracket 30. The gingival surface of the head 46 of the stem 42 can also abut the occlusal tips of the tie wings 32 of the bracket 30 to provide further support in terms of angulation. The head 46 has a horizontal passageway 48 that remains outside of the vertical slot 36.

Figure 7:
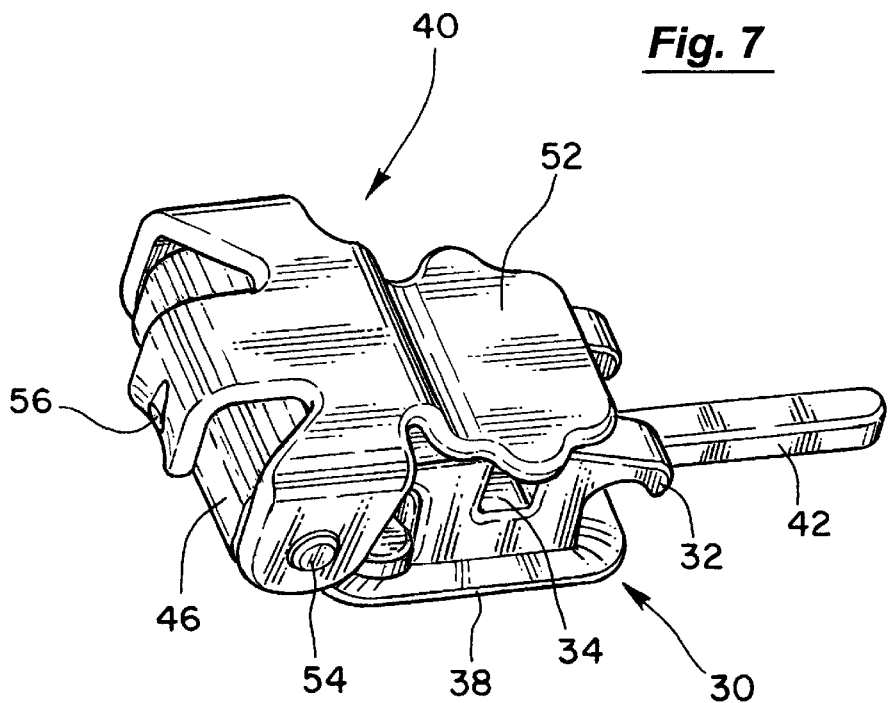
FIG. 7 is a perspective view of the self-ligating module 40 inserted into a bracket 30 with the pivoting spring clip 52 in its closed position.
Figure 8:
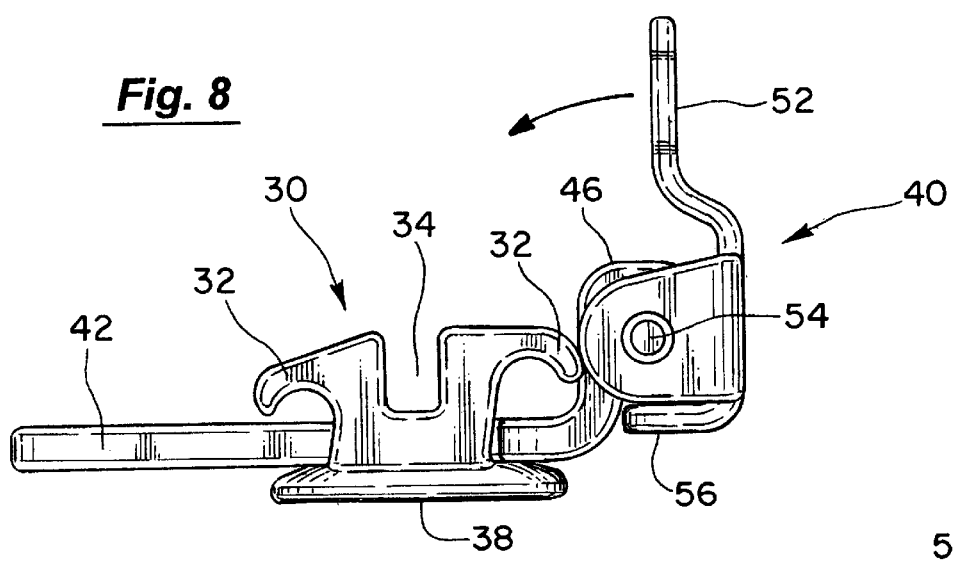
FIG. 8 is a side elevational view of the bracket 30 and self-ligating module 40 in the open position.
Figure 9:
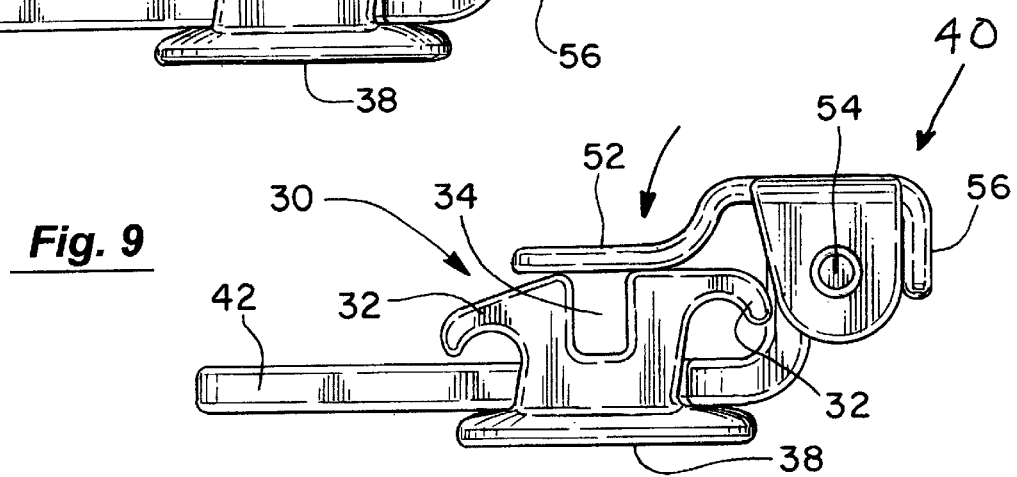
FIG. 9 is a side elevational view of the bracket 30 and self-ligating module 40 in the closed position corresponding to FIG. 7.

The pivoting spring clip 52 has a hinge pin 54 that extends through the horizontal passageway 48 in the head 46. This enables the clip 52 to pivot between an open position in which the archwire slot 34 is open to receive an archwire 20, as shown in FIG. 6, and a closed position in which the archwire 20 is secured in the archwire slot 34 by the clip 52, as shown in FIG. 7. FIGS. 8 and 9 are corresponding side elevational views of the bracket 30 and self-ligating module 40 in the open position and closed position, respectively.

Other means could be substituted for pivotably connecting the clip 52 to the head 46 of the stem 42. For example, the head could be equipped with a hinge pin that extends through a passageway in the clip. The hinge pin and passageway could also be replaced with complementary sets of indents and detents on the clip and head. The clip and head could also be formed as single piece with a live hinge.

A spring member 56 on the clip 52 contacts the head 46 and exerts a moment about the hinge pin 54 that either biases the clip 52 in an open position, or holds the archwire 20 in the archwire slot 34 in the closed position. In the preferred embodiment, the spring member 56 is centrally located on the occlusal aspect of the clip 52 when viewed in the closed position as illustrated in FIG. 9. The head 46 has lingual and occlusal facets that are relatively flat, but are separated by a rounded corner having a larger radius from the axis of rotation of the clip 52. The spring member 56 contacts the lingual facet of the head 46 to exert a biasing force holding the clip 52 in an open position, as shown in FIGS. 6 and 8. When the clip 52 is rotated to the closed position, the spring member 56 contacts the occlusal side of the head 46 to exert a biasing force holding the archwire 20 in the archwire slot 34, as shown in FIGS. 7 and 9. However, the rounded corner between the lingual and occlusal facet of the head 46 requires extra effort to overcome, and therefore tends to keep the clip 52 either in the open or closed position.

For a full understanding of the present invention, it must be understood that the self-ligating module 40 can be installed when needed, and then removed at any time by an orthodontist. The presence of the module 40 in a bracket 30 provides treatment options when needed, and after such a treatment objective has been accomplished, it can be easily and quickly removed. U.S. Pat. No. 4,975,052 (Spencer et. al.) discloses a space-closing methodology and cuspid retracting devices that can usefully inter-work with such a module. According to the present invention, the self-ligating module 40 as described above, in combination with a conventional orthodontic bracket 30 containing a vertical slot 36, through the addition of the pivoting spring clip 52 provide all of the self-ligation capabilities of current self-ligating brackets, yet can be removed as a unit from an otherwise conventional orthodontic bracket 30.

The above disclosure sets forth a number of embodiments of the present invention. Other arrangements or embodiments, not precisely set forth, could be practiced under the teachings of the present invention and as set forth in the following claims.

I claim:

1. A self-ligating module for removable attachment to an orthodontic bracket having an archwire slot to receive an archwire and a vertical slot extending through the bracket, said self-ligating module comprising:
    (a) a stem removably securable in the vertical slot in the bracket and having a head;
    (b) a clip pivotably secured to the head, said clip pivoting between an open position in which the archwire slot is open to receive an archwire, and a closed position in which the archwire is secured in the archwire slot by the clip; and
    (c) a spring member exerting a moment between the clip and the head of the stem to bias the clip in the closed position.

2. The removable self-ligating module of claim 1 wherein the stem further comprises an end passing through the vertical slot and wherein the clip is removably secured to the bracket by bending the end of the stem extending beyond the vertical slot.

3. The removable self-ligating module of claim 1 wherein the spring member also biases the clip in the open position.

4. The removable self-ligating module of claim 1 wherein the clip covers at least a portion of the archwire slot of the bracket in the closed position.

5. The removable self-ligating module of claim 1 wherein the head further comprises a horizontal passageway, and wherein the clip further comprises a hinge pin extending through the horizontal passageway in the head.

6. A removable self-ligating module for attachment to an orthodontic bracket having archwire slot to receive an archwire and a vertical slot extending through the bracket, said removable self-ligating module comprising:
    a stem removably securable in the vertical slot in the bracket and having a head with a horizontal passageway remaining outside of the vertical slot; and
    a clip having:
        (a) a hinge pin extending through the horizontal passageway in the head enabling the clip to pivot between an open position in which the archwire slot is open to receive an archwire, and a closed position in which the archwire is secured in the archwire slot of the bracket by the clip; and
        (b) a spring member contacting the head to exert a moment between the clip and the head of the stem and thereby bias the clip in the closed position.

7. The removable self-ligating module of claim 6 wherein the stem further comprises an end passing through the vertical slot and wherein the clip is removably secured to the bracket by bending the end of the stem extending beyond the vertical slot.

8. The removable self-ligating module of claim 6 wherein the clip covers at least a portion of the archwire slot of the bracket in the closed position.

* * * * *